United States Patent
Fogel et al.

(10) Patent No.: US 8,273,034 B2
(45) Date of Patent: Sep. 25, 2012

(54) METHOD AND DEVICE FOR TINNITUS MASKING

(75) Inventors: David B. Fogel, San Diego, CA (US); Gary B. Fogel, San Diego, CA (US)

(73) Assignee: Natural Selection, Inc., San Diego, CA (US)

( * ) Notice: Subject to any disclaimer, the term of this patent is extended or adjusted under 35 U.S.C. 154(b) by 797 days.

(21) Appl. No.: 12/297,435

(22) PCT Filed: Apr. 17, 2007

(86) PCT No.: PCT/US2007/066803
§ 371 (c)(1),
(2), (4) Date: Oct. 16, 2008

(87) PCT Pub. No.: WO2007/121446
PCT Pub. Date: Oct. 25, 2007

(65) Prior Publication Data
US 2009/0099476 A1    Apr. 16, 2009

Related U.S. Application Data

(60) Provisional application No. 60/792,828, filed on Apr. 17, 2006.

(51) Int. Cl.
*A61B 5/00* (2006.01)
*A61B 5/12* (2006.01)

(52) U.S. Cl. .......................................... 600/559; 73/585
(58) Field of Classification Search .................. 600/559, 600/25; 381/73.1, 312
See application file for complete search history.

(56) References Cited

U.S. PATENT DOCUMENTS

| 6,682,472 B1 | 1/2004 | Davis |
| 2004/0141624 A1 | 7/2004 | Davis et al. |

OTHER PUBLICATIONS

Notification of transmittal of the international search report and the written opinion of the international searching authority, International search report, Written opinion of the international searching authority, date of mailing Jun. 24, 2008, for International App. No. PCT/US07/66803, 9 pages.
Notification concerning transmittal of international preliminary report on patentability, and International preliminary report on patentability, date of mailing Oct. 30, 2008, for International App. No. PCT/US2007/066803, 6 pages.

*Primary Examiner* — Brian Szmal
(74) *Attorney, Agent, or Firm* — Law Office of Gerald Maliszewski; Gerald Maliszewski (57) ABSTRACT

A method for generating optimized tinnitus masks includes, for example, presenting stimuli in succession to a user, receiving the user's rating of the effectiveness of each presented stimulus in reducing tinnitus, selecting a subset of the stimuli to maintain as tinnitus masks, and, generating variant stimuli from the subset of the stimuli that is maintained as tinnitus masks.

92 Claims, 4 Drawing Sheets

METHOD AND DEVICE FOR TINNITUS MASKING

CROSS-REFERENCE TO RELATED APPLICATION

This application claims the benefit of U.S. Provisional Patent Application No. 60/792,828 filed Apr. 17, 2006, titled, "Method and device for tinnitus masking", which is incorporated herein by this reference.

BACKGROUND

1. Technical Field

The present invention relates to reduction of tinnitus suffering. More particularly, examples of the invention provide a novel method and device for optimization of maskings for the reduction of tinnitus suffering.

2. Description of Related Art

The American Tinnitus Association defines tinnitus as the term used generally to describe noises that are perceived in the absence of any true external source. Although some people suffer from what is called "objective tinnitus," in which there is an audible source for the noise that the person hears that can also be heard by another person, most people who suffer from tinnitus have "subjective tinnitus," in which the noises heard are not audible by anyone else.

Perhaps the most common form of tinnitus is described as a "ringing" in the ears, which may take on a specific tone, that is, an amplitude at a specific frequency, much like a tone generated by a tuning fork; however, tinnitus sufferers can hear other noises, which may be characterized by hissing, whooshing, buzzing, popping, or other terms. The volume of the noise may vary with head motion, physical activity, degree of consciousness, or other factors. For example, some people perceive a spike in a background level of tinnitus during the time that they begin to fall asleep or just after waking. Tinnitus can be associated with hearing loss, although this is not always the case, and can also be associated with medical conditions such as Meniere's disease or other auditory diseases, although this is also not always the case.

Tinnitus is a common ailment. It affects both adults and children. Currently, there is no definitive understanding of any genetic predisposition to tinnitus, although there are genetic predispositions to certain syndromes and medical conditions that are often associated with tinnitus. Many famous people have been afflicted with tinnitus, including reportedly musicians Neil Young, Pete Townshend, comedian David Letterman, and former president Ronald Reagan.

It is estimated that about 20 percent of all people suffer some degree of tinnitus (http://www.bixby.org/faq/tinnitus/discover.html). The National Institute on Deafness and Other Communication Disorders (NIDOCD) (which is part of the National Institutes of Health) reports that over 12 million Americans suffer from tinnitus. The American Academy of Otolaryngology reports that 36 million Americans suffer from tinnitus. The American Tinnitus Association and Society for Neuroscience report that over 50 million Americans are afflicted with this condition. Dr. Pawel Jastreboff reported that over 4 million Americans suffer significantly from tinnitus.

It has been reported that in a study of over 1544 tinnitus patients, over three-quarters of these patients characterized tinnitus sounds as being "tonal" with an mean degree of loudness of 7.5 on subjective 10 scale (http://www.bixby.org/faq/tinnitus/discover.html). Of the remainder 21 percent characterized the sound with a mean loudness of 5.5. For comparison, an externally generated noise source was 7.5 dB above threshold, and a majority of patients could have their tinnitus masked by sounds that were 14 dB above threshold. Most persons described their tinnitus as being located in both ears, but others described it as emanating from the head, or only one ear. The American Tinnitus Association reported that there was no statistical correlation, however, between the measured level of tinnitus and the sufferers perception of the severity of the tinnitus. Tinnitus is a very personal and subjective experience.

Noise exposure has been identified as a source for causing tinnitus, particularly heavy construction equipment, leaf blowers, jet engines, rock concerts, and similar sources, but in a study of 1687 tinnitus patients, no known cause was identified for 43 percent of the cases (http://www.bixby.org/faq/tinnitus/discover.html). It is often very difficult to determine the source of tinnitus and the mechanisms involved are not completely or even well understood in many cases. There is some evidence to suggest that specific foods may cause tinnitus, including red wine and other alcohol, cheese, caffeine, tonic water, and chocolate, and there have been reported similarities to foods that cause migraines. Artificial sweeteners such as aspartame have been claimed (but perhaps not proven) to be associated with tinnitus, and aspirin is associated with some cases of tinnitus (although there is less agreement about the effects of other non-steroidal anti-inflammatory NSAID drugs). Other drugs, such as oral contraceptives and nicotine, may also be associated with bringing on or worsening cases of tinnitus. The NIDOCD reports that over 200 medicines are associated with causing tinnitus.

Various diseases are also associated with tinnitus, including lyme disease, acoustic neuromas, glomous tumors (which may cause pulsatile tinnitus), and otosclerosis. Medical conditions may also contribute to tinnitus, including ear wax build up, ear infections, suffering from a flu or other virus or other infection, TMJ syndrome, certain tumors, fibromyalgia, high blood cholesterol levels, and hypertension. Injuries such as head trauma and dental procedures have been associated with tinnitus. Some people have indicated that mercury amalgam tooth fillings may be associated with tinnitus, but these claims are at best controversial. Other conditions such as stress, fatigue, and diet have also been associated with episodes of tinnitus.

Various medical tests and procedures have been created for determining a diagnosis of tinnitus; however, tinnitus sufferers generally do not need specific tests to diagnose that they are hearing noises. Such tests may be helpful in identifying particular types of tinnitus, but may not be helpful in addressing the symptoms of the condition, that is, such tests may not be helpful in alleviating, mediating, or halting the sensation of hearing noises.

The treatments for tinnitus are quite varied, with no true cure for the condition. Some drug treatments include the use of anti-depressants and anti-anxiety medications. Tinnitus sufferers may become depressed or feel tense from the constant noise that they hear. The medications may help sufferers to cope with the tinnitus but do not cure the condition, although some reports have indicated that these medications may reduce the level of tinnitus, perhaps with some physiologically reasonable rationale (that is, other than a placebo effect). Some of the drugs in these classes of medicines may also increase tinnitus.

Dr. Robert M. Johnson et al. reported on a double-blind study with a placebo control for administering alprazolam (marketed as Xanax) in which over three-quarters of subjects reported a reduction in tinnitus of at least 40 percent. This compared well to only 5 percent of the placebo subjects with an improvement in tinnitus. Xanax, and other drugs in this class, can be addicting and have other side effects, and so this treatment has important deficiencies. Other drug treatments reported in the literature have included anti-convulsants, local anesthetics, anti-arrhythmics, histamine, anti-histamine, and diuretics. Each of these carries potential side effects and none is entirely effective.

Herbs and vitamins have also been explored to alleviate tinnitus. Some evidence has suggested a possible vitamin B-12 deficiency in some tinnitus sufferers. Vasodilators such as niacin or *Gingko biloba* have been tested. The results may be described as inconclusive, with some theoretical justification for believing that vasodilators may make tinnitus worse in certain patients. Also high doses of niacin are associated with flushing and also potentially liver damage, and *Gingko biloba* is a blood thinner, which may not be appropriate for some patients. Zinc has also been suggested as possibly beneficial, but high levels of zinc may interfere with copper absorption. Magnesium has been tested on tinnitus sufferers that were exposed to high levels of impulse noises (for example, explosions). Hearing loss was reduced by the administering of magnesium, however the effect on tinnitus was not entirely clear.

Other efforts to reduce or halt tinnitus include hypnosis, chiropractic adjustment, biofeedback, relaxation, counseling, self-help group therapy, acupuncture, hearing aids (used more to improve the signal-to-noise ratio of people talking as compared to the level of tinnitus than to reduce the level of tinnitus), oxygen therapy, and electrical stimulation of the ear. None of these methods have established clinically verifiable repeatable effectiveness on a broad spectrum of tinnitus sufferers. It is noteworthy that severing the auditory nerves of a tinnitus sufferer, which leaves the sufferer completely deaf, may not alleviate tinnitus. If tinnitus is originating in the brain, the sufferer may still continue to hear the sounds, even though he or she cannot hear anything else.

One of the more interesting approaches to addressing tinnitus is described as "auditory integration training" (AIT). Studies by Dr. Guy Berard (reported in *Hearing Equals Behavior*) have reported the method of listening to music that is altered such that high and low frequencies are randomly shifted in and out. The course of treatment is reported as 30 minute sessions, twice per day, for 10 days. Two different devices have been constructed for delivering the Berard AIT. At this time, reports suggest that there is no scientifically proven theory for why AIT should work but it is reported to be potentially effective. Some concerns have been indicated that AIT treatments may be given at uncomfortably loud volume levels, which could worsen tinnitus. Several AIT organizations are currently in operation in the United States of America. It has been reported that professional memberships in at least one organization have been suspended pending FDA approval of the AIT devices. Similarly, sound therapy can be offered to a tinnitus sufferer, which generally involves listening to constantly alternating sounds of high and low tone. Simultaneously, low frequency sounds are progressively removed so the ear is introduced to higher and higher frequencies. Reduction in tinnitus is reported as occurring in as little as 24 hours or as long as 14 months. In tinnitus retraining therapy, reported results may take as long as 18 months.

Another approach to treating tinnitus is to mask the tinnitus with other noises. A common noise used for this purpose is white noise, akin to radio static; however, many other sources of noise can be used including filtered white noise (that is, white noise that is altered by mathematical filters to have different spectral properties), rain, waterfalls, surf, airplane cabin sounds, and others. The concept of masking is to provide the brain with an external source of noise that serves as a distraction from the tinnitus. A common way to describe this is that the brain would rather listen to real noises than imaginary noises, and thus these sounds can reduce tinnitus, sometimes greatly and even all the way to a complete halting of the imagined noise. The trade-off that tinnitus sufferers must choose is whether it is easier to listen to the distraction noise or their tinnitus; however, in some cases, tinnitus sufferers have noted that by applying masking sounds, when the sounds are removed, the tinnitus does not return, or does not return for a significant amount of time, or continues but at a reduced level.

Products exist currently that serve the purpose of tinnitus masking. For example, Ambient Shapes, Inc. of Hickory, N.C. sells the Marsona Tinnitus Masker, which offers over 3000 alternative masking noises, for approximately $250. The Sharper Image company of San Francisco, Calif. offers two tinnitus masking devices, the Portable Sound Soother and the Digital Sound Soother, for $120 and $170, respectively. The devices offer alarm clocks and three sources of noise: white noise, seaside, and countryside. Additional independent sounds such as fog horns and owls are also included with independent volume control.

A deficiency of the masking approach is in finding the right noise to provide to the tinnitus sufferer. A trial-and-error process can be conducted by a third person, such as a hearing professional (a medical doctor trained as an otolaryngologist or a medical assistant), to determine which of a collection of noises might have the best effect (known as residual inhibition). This approach is much like the process that is used commonly to adjust eyeglass prescriptions, in which a third person allows an eyeglass wearer to look though alternative lenses and asks if their vision is better or worse, converging over a series of alterations on an optimum. In tinnitus retraining therapy, the process is reported to require extensive one-on-one time with highly trained professionals (although the process may not require masking noises but instead "enriching" the sound background, coupled with counseling). This is a deficiency that is addressed by the current invention.

Furthermore, unfortunately, the physics of hearing and of tinnitus, which may derive from brain activity and not from the auditory nerve, is not as simple as the physics of visual acuity. It is not true that a person can simply follow a progression of alternative forms of noise and arrive at an optimal form that provides maximum residual inhibition. In fact, the optimal static form may be a combination of other noises, not any single noise. Furthermore, with the idea of transforming noises presented to the tinnitus sufferer, as described above, the challenge becomes one of finding not just a best noise source to use, but a best noise source that changes over time. In addition, what may be the optimal source to use for a tinnitus patient on a given day or in a given background setting may not be optimal on another day or in a different background setting. These deficiencies are also addressed by the current invention.

SUMMARY

Some examples of the invention provide a method and device for alleviating or eliminating tinnitus in a user by allowing the user to generate personalized tinnitus masks. One aspect of the invention is a method for generating optimized tinnitus masks. An example of the method includes the operations of presenting stimuli in succession to a user, receiving the users rating of the effectiveness of each presented stimulus in reducing tinnitus, selecting a subset of the stimuli to maintain as tinnitus masks, and, generating variant stimuli from the subset of the stimuli that is maintained as tinnitus masks.

Other aspects of the invention are described in the sections below, and include, for example, a method for optimizing tinnitus masks, and a method for the collection and sharing of tinnitus masks. Computing system aspects of the invention, and computer readable medium aspects of the invention, are also described in the sections below.

One or more advantages may be provided by examples of the invention. For example, some examples of the invention advantageously generate optimized tinnitus masks. Further, some examples of the invention beneficially provide for the collection and sharing of tinnitus masks. The invention also provides a number of other advantages and benefits, which should be apparent from the following description.

DETAILED DESCRIPTION

The nature, objectives, and advantages of the invention will become more apparent to those skilled in the art after considering the following detailed description in connection with the accompanying drawings.

The following is a list of reference numerals in the drawings.

Figure 1:
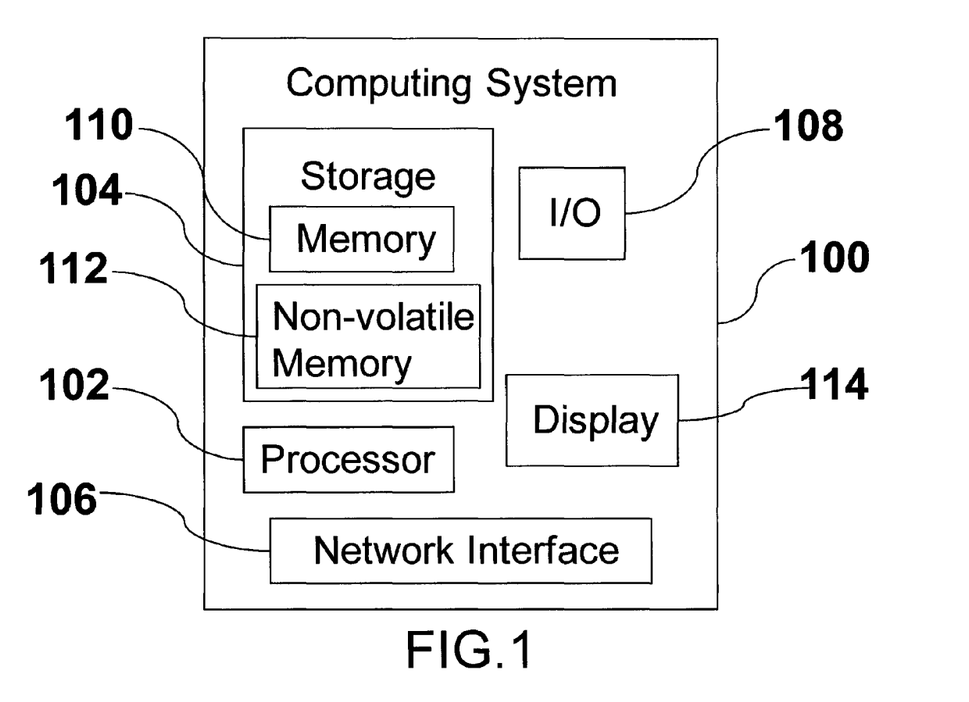
FIG. 1 is a block diagram of the hardware components and interconnections of a computing system in accordance with an example of the invention.
Figure 2:
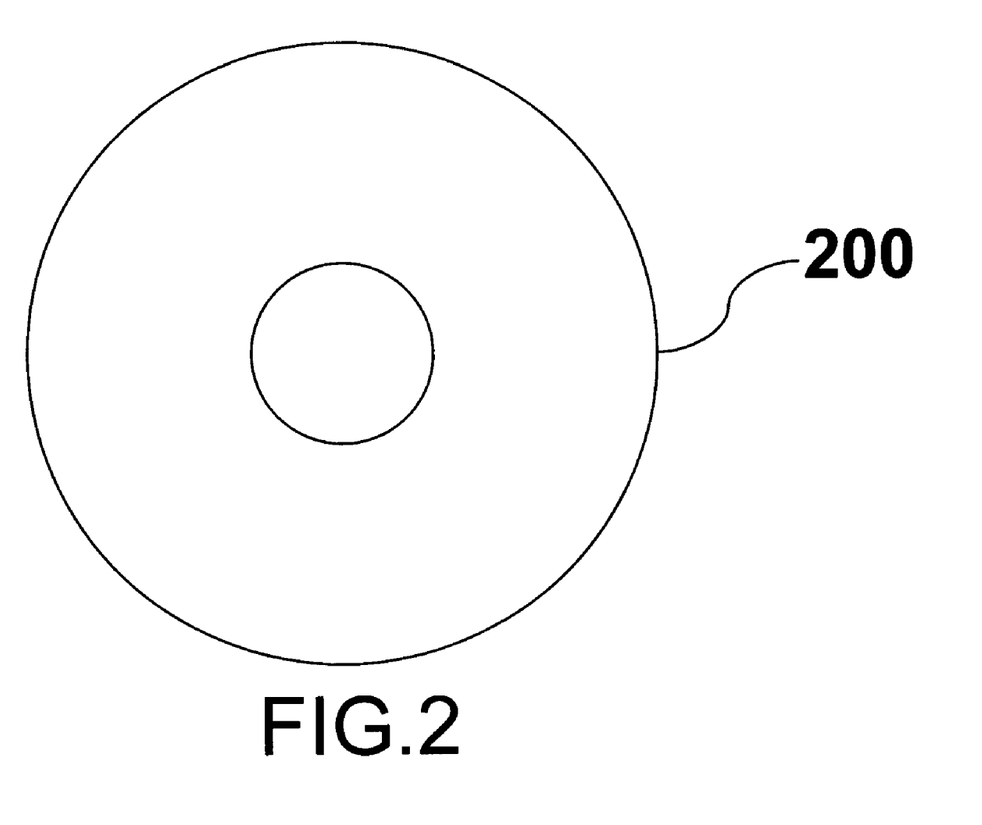
FIG. 2 is an example of a signal-bearing medium in accordance with an example of the invention.
Figure 3:
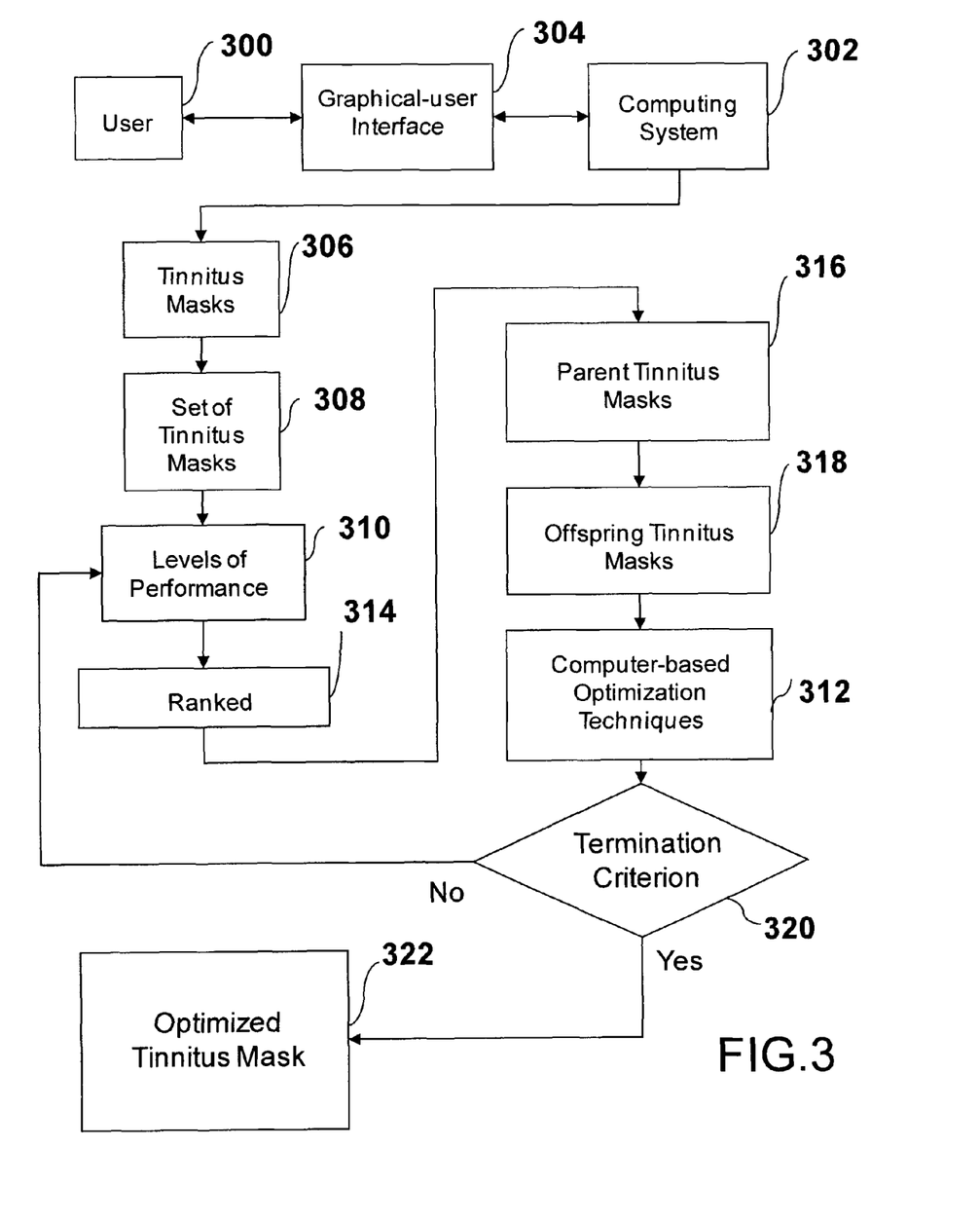
FIG. 3 is a block diagram of a method for generating optimized tinnitus masks in accordance with an illustrative embodiment of the invention.
Figure 4:
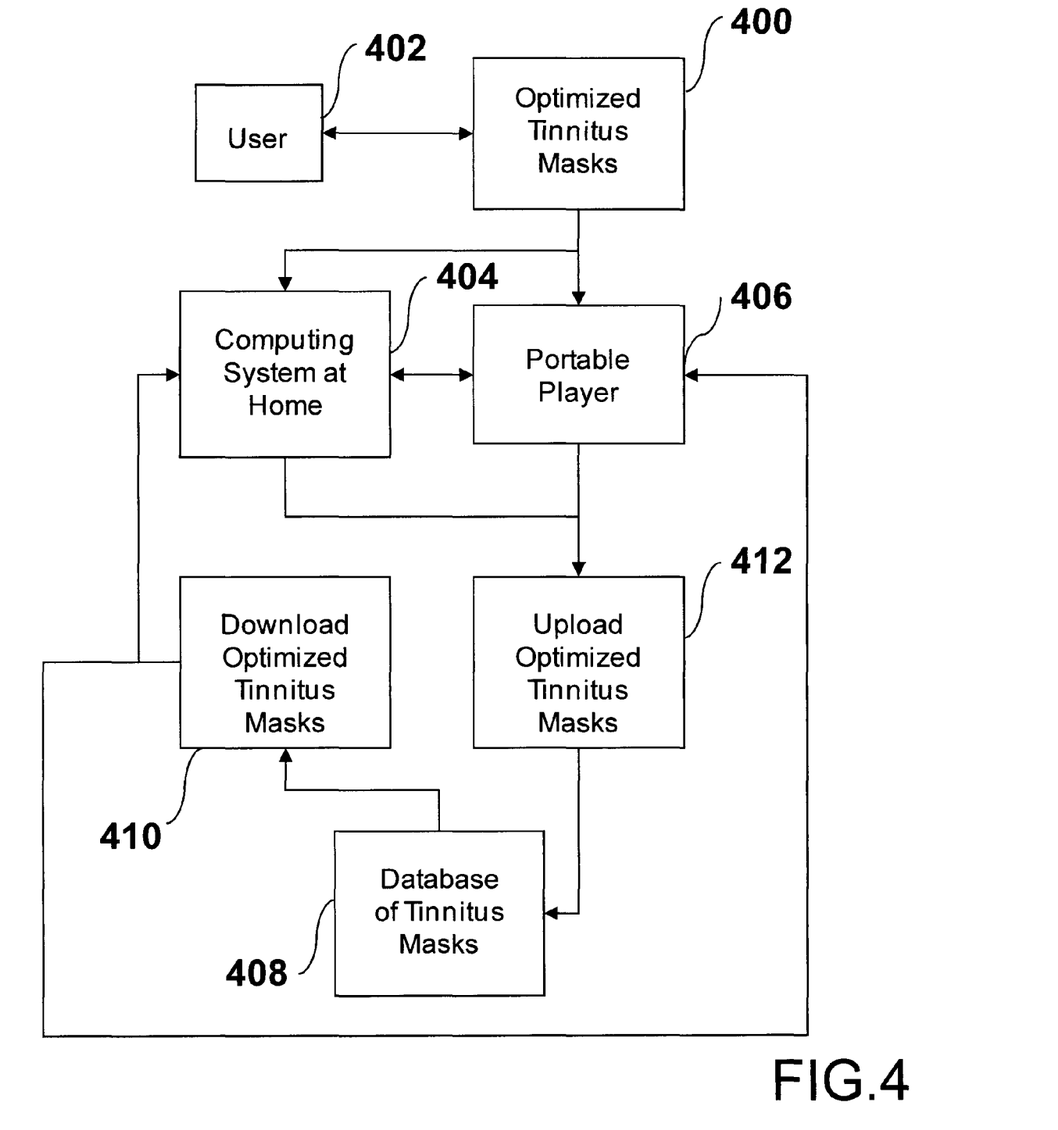
FIG. 4 is a block diagram of a method for using and sharing optimized tinnitus masks by a user, in accordance with an illustrative embodiment of the invention.

Reference Numerals in FIG. 1:
100 Computing system
102 Processor
104 Storage
106 Network interface
108 Input/output
110 Memory
112 Non-volatile memory
114 Display
  Reference Numerals in FIG. 2:
200 Optical storage disk
  Reference Numerals in FIG. 3:
300 User
302 Computing system
304 Graphical-user interface
306 Tinnitus masks
308 Set of tinnitus masks
310 Levels of performance
312 Computer-based optimization techniques
314 Ranked
316 Parent tinnitus masks
318 Offspring tinnitus masks
320 Termination criterion
322 Optimized tinnitus mask
  Reference Numerals in FIG. 4:
400 Optimized tinnitus masks
402 User
404 Computing system at home
406 Portable player
408 Database of tinnitus masks
410 Download optimized tinnitus masks
412 Upload optimized tinnitus masks

DESCRIPTION

Preferred Embodiment

A. Signal-Bearing Media

In the context of FIGS. 1 and 2, the method aspects of the invention may be implemented, for example, by having a computing system 100 containing a processor 102, execute a sequence of machine-readable instructions, which can also be referred to as code, for carrying out one or more examples of the invention or portions of the invention. These instructions may reside in various types of signal-bearing media containing a storage 104 which consists of memory 110 and/or non-volatile memory 112, with the potential for a network interface 106 and input/output (1/0) 108 for communication with other machines and/or data storage devices and/or humans and a display 114 for ease of human interpretation. In this respect, some aspects of the present invention concern a programmed product, comprising a signal-bearing medium or signal-bearing media tangibly embodying a program of machine-readable instructions executable by a digital processing apparatus to perform operations, for example, for generating optimized tinnitus masks, or for optimizing tinnitus masks, or for the collection and sharing of tinnitus masks.

This signal-bearing medium may comprise, for example, primary memory 110 and/or non-volatile memory 112. Alternatively, the instructions may be embodied in a signal-bearing medium such as the optical data storage disc 200 shown in FIG. 2. The optical disc can be any type of signal-bearing disc or disk, for example, a CD-ROM, CD-R, CD-RW, WORM, DVD-R, DVD+R, DVD-RW, or DVD+RW. Additionally, whether contained in the computing system 100, or elsewhere, the instructions may be stored on any of a variety of machine-readable data storage mediums or media, which may include, for example, a "hard disk drive", a RAID array, a magnetic data storage diskette (such as a floppy disk), magnetic tape, digital optical tape, RAM, ROM, EPROM, EEPROM, flash memory, programmable logic, any other type of firmware, magneto-optical storage, paper punch cards, or any other suitable signal-bearing media including transmission media such as digital and/or analog communications links, which may be electrical, optical, and/or wireless. For example, in some embodiments the instructions or code may be accessible from a file server over a network, or from other transmission media, and the signal-bearing media embodying the instructions or code may comprise a transmission media, such as a network transmission line, wireless transmission media, signals propagating through space, radio waves, and/or infrared signals. Alternatively, the signal-bearing media may be implemented in hardware logic, for example, an integrated circuit chip, a Programmable Gate Array (PGA), or an Application Specific Integrated Circuit (ASIC). As an example, the machine-readable instructions may comprise microcode, or may comprise software object code, compiled from a language such as "C++".

B. General Discussion of Operation

A preferred embodiment of the present invention is illustrated in FIGS. 3 and 4. A user 300 interacts with a computing system 302 for the purpose of optimizing tinnitus masks that are personalized to the user. The computing system contains a graphical-user interface 304 for the ease of utility and interpretation. Utilizing said graphical-user interface 304, tinnitus masks 306 are presented to the user 300. Said tinnitus masks are generated based on parameters on types of sounds such as low frequency sounds, high frequency sounds, variable-frequency sounds, airplane background noise, white noise, waterfall or other sounds from natural or unnatural settings. The parameters on the types of noises involve the volume and phase and frequency spectrum of each sound type such that the types of noises and their parameters can be adjusted. In addition, the tinnitus masks 306 may contain non-auditory stimulus such as visual, olfactory, or tactile as adjustable parameters. Using the graphical-user interface 304 the method generates a set of tinnitus masks 308 that contains different tinnitus masks 306 with associated parameters. The user then listens to each tinnitus mask 306 and rates the effectiveness of said masks at reducing the level of tinnitus suffered by the user 300. The tinnitus reduction is measured in terms of levels of performance 310 such as the level of tinnitus reduction experienced by the user while listening to the tinnitus mask 306, the level of tinnitus reduction experienced by the user after the tinnitus mask 306 has stopped playing, and the duration of the tinnitus reduction experienced, if any, in terms of time intervals such as less than 5 seconds, between 5 seconds and 30 seconds, between 30 seconds and 1 minute, between 1 minute and 5 minutes, between 5 minutes and 10 minutes, and so forth. Various computer-based optimization techniques 312 can then be called upon to optimize subsequent tinnitus masks 306 presented to the user 300, such as steepest gradient descent, simulated annealing, and heuristic methods. The preferred embodiment utilizes an optimization technique based on simulated Darwinian evolution. Given the user scoring of the evaluated tinnitus masks, said masks are ranked 314 in accordance with their worth to the user, with the best solutions retained to serve as parent tinnitus masks 316 for subsequent discovery and optimization of future tinnitus masks. Said tinnitus masks are randomly varied on their degrees of freedom such as their tinnitus mask parameters, thereby producing offspring tinnitus masks 318. Alternatively, variation in the tinnitus masks 306 can be established using an algorithm that determines a trend in the available data and produces new parameters that are likely to be in a favorable direction in parameter space. Alternatively, variation in the tinnitus profiles 306 can be established using some preprogrammed method for searching the parameter space. These offspring tinnitus masks and the remaining parent coefficient assignments form a new generation that is similarly scored by the user 300. A selection of most useful tinnitus masks is made and this process iterates until tinnitus masks optimized to the user have been generated, or a condition that satisfies a termination criterion 320 has been reached. The optimized tinnitus mask 322 can then be utilized by the user 300 for reduction of tinnitus suffering.

In the context of FIG. 4, the optimized tinnitus masks 400 discovered by a user 402 can be played on a computing system at home 404 or downloaded in MP3 or other format to a portable player 406 such as a laptop, MP3 player, or other device that allows the user to transport the optimized tinnitus masks 400 for use whenever tinnitus affects the user 402. The user can upload optimized tinnitus masks 400 to a database of tinnitus masks 408 for sharing with other tinnitus sufferers. The database is accessed via a fee-for-service business model, which retains rights to the best tinnitus masks discovered with this approach but allows users to upload optimized tinnitus masks 410 or download optimized tinnitus masks 412 developed by other sufferers. The user can also download specific or a random choice of optimized tinnitus masks from the database of tinnitus masks 410 for use in the optimization of personalized tinnitus masks so that information contained in the database can be used to accelerate the search for personalized tools that alleviate suffering.

Operation—FIG. 3 and FIG. 4

As an example of the operation of the preferred embodiment, a tinnitus sufferer interacts with the method and device through a graphical-user interface in order to optimize a tinnitus mask that is personal and works over as long a duration as possible during and subsequent to the application of the tinnitus mask. Potential stimuli such as white noise are selected by the user. The phase, volume, and other parameters associated with white noise are adjusted by the user. This particular white noise tinnitus mask is then played in succession along with others generated by the user or method to the user via speakers or headphones or other auditory device associated with the computing system. The user rates the effectiveness of each tinnitus mask on its ability to alleviate tinnitus suffering in some regard, either while the tinnitus mask was being played or after the tinnitus mask has ended or both. The set of tinnitus masks is then ranked according to the user evaluation and a selection of a subset of the stimuli, for instance the top half of the available tinnitus masks, is chosen to serve as parent tinnitus masks for a subsequent generation of optimization. Variation is used to generate new tinnitus masks for the set of tinnitus masks. The variation process can be automated as part of the optimization process or derived by the user. These offspring tinnitus masks are then included in the set of tinnitus masks and re-evaluated by the user for their ability to alleviate tinnitus suffering. For example on the second round of evaluation, the previous white noise stimuli might be adjusted in pitch and volume to present an even better tinnitus mask to the user. Further rounds of pitch, volume, and duration alteration lead to optimized masks in light of the personal requirements of the user.

The following entries describe examples of various aspects the invention:

Entry 1. A method for generating optimized tinnitus masks consisting of the steps:
 a. identification of potential stimuli to a user to alleviate tinnitus
 b. identification of parameters for each stimulus that modify said stimulus
 c. specific stimuli are presented to the user in succession
 d. the user rates the effective of each of the stimuli in terms of tinnitus reduction
 e. selection of a subset of the stimuli to maintain as tinnitus masks
 f. generation of variant stimuli from the subset that is maintained
 g. generation of new stimuli
 h. user repeats operation of presentation of stimuli and rating on effectiveness.

Entry 2. A method for the optimization of tinnitus masks including:
 i. parent tinnitus masks
 j. a process of variation
 k. offspring tinnitus masks
 l. a means of scoring the worth or fitness of alternative tinnitus masks
 m. a means of selection
 n. a termination criterion as a decision gate for the termination or iteration of the process.

Entry 3. A method for the collection and sharing of tinnitus masks including:
 o. a means for uploading tinnitus masks
 p. a means for downloading tinnitus masks
 q. a means for uploading personal information
 r. a fee for service.

Entry 4. The method of entry 1 where the potential stimuli include sounds.

Entry 5. The method of entry 4 where the sounds include white noise, spectrally adjusted noise, sounds from natural settings, sounds from man-made objects, and tones.

Entry 6. The method of entry 1 where the parameters for each stimulus include frequency information, volume, phase information, and each of those as a function of time and also duration.

Entry 7. The method of entry 1 where the succession of stimuli are presented via a graphical-user interface.

Entry 8. The method of entry 1 where the user rates the performance of tinnitus masks via a graphical-user interface.

Entry 9. The method of entry 1 where the user rates tinnitus reduction in terms of parameters including reduction of tinnitus while the stimulus is being presented, reduction of tinnitus after the stimulus is presented, duration of the tinnitus reduction after termination of the tinnitus mask.

Entry 10. The method of entry 1 where selection is made based on the rank-ordered preference of the user.

Entry 11. The method of entry 1 where the generation of variant stimuli is based on random variation of parent tinnitus masks, directed variation of parent tinnitus masks, introduction of new tinnitus masks, re-introduction of old tinnitus masks, or downloading of tinnitus masks from a database.

Entry 12. The method of entry 1 where the generation of variant stimuli is user derived based upon tinnitus masks presented to the user.

Entry 13. The method of entry 2 where the generation of tinnitus masks is based on random variation of parent tinnitus masks, directed variation of parent tinnitus masks, introduction of new tinnitus masks, re-introduction of old tinnitus masks, or downloading of tinnitus masks from a database.

Entry 14. The method of entry 2 where the generation of variant stimuli is user derived based upon tinnitus masks presented to the user.

Entry 15. The method of entry 2 where a process of variation consists of methods of modification of tinnitus masks using a distribution such as a Gaussian function.

Entry 16. The method of entry 2 where a process of variation consists of methods of modification of the tinnitus masks in terms of combining parts of two or more existing tinnitus masks or one or more tinnitus masks with one or more other tinnitus masks.

Entry 17. The method of entry 13 where the process of combining includes taking discrete parts of the tinnitus mask, averaging across tinnitus masks, or generating a new tinnitus mask or masks based on a function of existing tinnitus masks or one or more tinnitus masks with existing tinnitus masks.

Entry 18. The method of entry 2 where self-adaptation of the evolutionary parameters associated with evolution of tinnitus masks is used to optimize performance.

Entry 19. A device for implementing the method of entry 1, consisting of a computing machine to store the possible tinnitus masks and algorithms implemented on computing machines for searching through tinnitus masks, and a selective method of choosing which tinnitus masks are to be favored.

Other Embodiments

A number of illustrative embodiments of the invention have been described herein. It will be apparent to persons skilled in the art that various changes and modifications can be made to the described embodiments without departing from the scope of the invention as defined by the following claims.

What is claimed is:

1. A method for generating optimized tinnitus masks, the method comprising the following operations:
   presenting stimuli in succession to a user;
   receiving the user's rating of the effectiveness of each presented stimulus in reducing tinnitus;
   selecting a subset of the stimuli to maintain as tinnitus masks;
   generating variant stimuli from the subset of the stimuli that is maintained as tinnitus masks;
   storing the tinnitus masks generated from the subset of stimuli in a non-transitory memory medium of a secondary device; and,
   supplying the tinnitus masks from the secondary device.

2. The method of claim 1, wherein the presented stimuli include sounds.

3. The method of claim 2, wherein the sounds include white noise, spectrally adjusted noise, sounds from natural settings, sounds from man-made objects, and tones.

4. The method of claim 1, wherein the presented stimuli include stimulus comprising white noise.

5. The method of claim 1, wherein the presented stimuli include stimulus comprising spectrally adjusted noise.

6. The method of claim 1, wherein the presented stimuli include stimulus comprising sounds from natural settings.

7. The method of claim 1, wherein the presented stimuli include stimulus comprising sounds from man-made objects.

8. The method of claim 1, wherein the presented stimuli include stimulus comprising tones.

9. The method of claim 1, wherein the presented stimuli include stimulus comprising low frequency sounds.

10. The method of claim 1, wherein the presented stimuli include stimulus comprising high frequency sounds.

11. The method of claim 1, wherein the presented stimuli include stimulus comprising variable-frequency sounds.

12. The method of claim 1, wherein the presented stimuli include stimulus comprising airplane background noise.

13. The method of claim 1, wherein the presented stimuli include stimulus comprising waterfall sounds.

14. The method of claim 2, wherein the presented stimuli include visual stimulus.

15. The method of claim 2, wherein the presented stimuli include olfactory stimulus.

16. The method of claim 2, wherein the presented stimuli include tactile stimulus.

17. The method of claim 1, wherein each presented stimuli is different than each other presented stimuli.

18. The method of claim 1, wherein the operations further comprise identifying potential stimuli for alleviating tinnitus.

19. The method of claim 18, wherein the operations further comprise identifying parameters associated with each identified potential stimulus, wherein the associated parameters can be adjusted to modify the respective identified potential stimulus.

20. The method of claim 1, wherein the operations further comprise selecting the stimuli to be presented to the user.

21. The method of claim 20, wherein the user performs the operation of selecting the stimuli to be presented to the user.

22. The method of claim 1, wherein the operations further comprise adjusting parameters associated with the stimuli to be presented to the user.

23. The method of claim 22, wherein the user performs the operation of adjusting parameters associated with the stimuli to be presented to the user.

24. The method of claim 1, wherein the presented stimuli are stimuli that have been selected by the user, and wherein the presented stimuli have associated parameters that have been adjusted by the user.

25. The method of claim 1, wherein the user's rating of the effectiveness of each presented stimulus includes the user's rating of the tinnitus reduction experienced by the user while listening to the respective stimulus.

26. The method of claim 1, wherein the user's rating of the effectiveness of each presented stimulus includes the user's rating of the tinnitus reduction experienced by the user after the respective stimulus has stopped.

27. The method of claim 1, wherein the user's rating of the effectiveness of each presented stimulus includes the user's rating of the duration of the tinnitus reduction after the respective stimulus has stopped.

28. The method of claim 1, wherein the user's rating of the effectiveness of each presented stimulus includes the user's rating of the tinnitus reduction experienced by the user in a time interval less than 5 seconds after the respective stimulus has stopped.

29. The method of claim 1, wherein the user's rating of the effectiveness of each presented stimulus includes the user's rating of the tinnitus reduction experienced by the user in a time interval between 5 seconds and 30 seconds after the respective stimulus has stopped.

30. The method of claim 1, wherein the user's rating of the effectiveness of each presented stimulus includes the user's rating of the tinnitus reduction experienced by the user in a time interval between 30 seconds and 1 minute after the respective stimulus has stopped.

31. The method of claim 1, wherein the user's rating of the effectiveness of each presented stimulus includes the user's rating of the tinnitus reduction experienced by the user in a time interval between 1 minute and 5 minutes after the respective stimulus has stopped.

32. The method of claim 1, wherein the user's rating of the effectiveness of each presented stimulus includes the user's rating of the tinnitus reduction experienced by the user in a time interval between 5 minutes and 10 minutes after the respective stimulus has stopped.

33. The method of claim 1, wherein the operations further comprise ranking the presented stimuli in accordance with the user's ratings of the presented stimuli.

34. The method of claim 1, wherein the subset of the stimuli that is selected to maintain as tinnitus masks is selected based on a rank-ordering of the presented stimuli in accordance with the user's ratings of the presented stimuli.

35. The method of claim 1, wherein the operations further comprise ranking the presented stimuli in accordance with the user's ratings of the presented stimuli, and wherein the operation of selecting a subset of the stimuli to maintain as tinnitus masks comprises selecting a portion of the ranked stimuli.

36. The method of claim 1, wherein each presented stimulus has associated parameters.

37. The method of claim 1, wherein the operation of generating variant stimuli comprises varying a parameter of each stimulus in the subset of the stimuli that is maintained as tinnitus masks.

38. The method of claim 1, wherein the operation of generating variant stimuli comprises varying at least one parameter of each stimulus in the subset of the stimuli that is maintained as tinnitus masks.

39. The method of claim 1, wherein the operation of generating variant stimuli comprises varying a plurality of parameters of each stimulus in the subset of the stimuli that is maintained as tinnitus masks.

40. The method of claim 37, wherein the varied parameters are varied randomly.

41. The method of claim 1, wherein the operation of generating variant stimuli comprises randomly varying parameters of the stimuli in the subset of the stimuli that is maintained as tinnitus masks.

42. The method of claim 1, wherein the operation of generating variant stimuli comprises using an algorithm that determines a trend in available data and produces new stimuli parameter values that are likely to be in a favorable direction in parameter space.

43. The method of claim 1, wherein the operation of generating variant stimuli comprises using a steepest gradient descent computer-based optimization technique to produce new stimuli parameter values.

44. The method of claim 1, wherein the operation of generating variant stimuli comprises using a simulated annealing computer-based optimization technique to produce new stimuli parameter values.

45. The method of claim 1, wherein the operation of generating variant stimuli comprises using a simulated evolution optimization technique to produce new stimuli parameter values.

46. The method of claim 1, wherein the operation of generating variant stimuli comprises varying a volume parameter of a stimulus in the subset of the stimuli that is maintained as tinnitus masks.

47. The method of claim 1, wherein the operation of generating variant stimuli comprises varying a phase parameter of a stimulus in the subset of the stimuli that is maintained as tinnitus masks.

48. The method of claim 1, wherein the operation of generating variant stimuli comprises varying a frequency spectrum parameter of a stimulus in the subset of the stimuli that is maintained as tinnitus masks.

49. The method of claim 1, wherein the operation of generating variant stimuli comprises varying a pitch parameter of a stimulus in the subset of the stimuli that is maintained as tinnitus masks.

50. The method of claim 1, wherein the operation of generating variant stimuli comprises varying a duration parameter of a stimulus in the subset of the stimuli that is maintained as tinnitus masks.

51. The method of claim 1, wherein each presented stimulus has associated parameters including frequency information, volume, and phase information.

52. The method of claim 1, wherein each presented stimulus has associated parameters that can be varied, including frequency information as a function of time, volume as a function of time, and phase information as a function of time.

53. The method of claim 1, wherein each presented stimulus has associated parameters that can be adjusted, including frequency information as a function of duration, volume as a function of duration, and phase information as a function of duration.

54. The method of claim 1, wherein the operation of generating variant stimuli comprises randomly varying parent tinnitus masks.

55. The method of claim 1, wherein the operation of generating variant stimuli comprises directing the variation of parent tinnitus masks.

56. The method of claim 1, wherein the operation of generating variant stimuli comprises introducing new tinnitus masks.

57. The method of claim 1, wherein the operation of generating variant stimuli comprises reintroducing old tinnitus masks.

58. The method of claim 1, wherein the operation of generating variant stimuli comprises downloading tinnitus masks from a database.

59. The method of claim 1, wherein the operation of generating variant stimuli is user derived based upon tinnitus masks presented to the user.

60. The method of claim 1, wherein the operations further comprise presenting the variant stimuli in succession to the user.

61. The method of claim 60, wherein the operations further comprise:
receiving the user's rating of the effectiveness of each presented variant stimulus in reducing tinnitus;
selecting a subset of the variant stimuli to maintain as additional tinnitus masks; and
generating new variant stimuli from the subset of the variant stimuli that is maintained as additional tinnitus masks.

62. The method of claim 1, wherein the operations further comprise:
presenting the subset of the stimuli maintained as tinnitus masks, and the variant stimuli, in succession to the user;
receiving the user's rating of the effectiveness of each stimulus maintained as a tinnitus mask, and each variant stimulus, in reducing tinnitus;
selecting a subset of the presented stimuli maintained as tinnitus masks, and the presented variant stimuli, to maintain as a new set of tinnitus masks; and
generating new variant stimuli from the new set of tinnitus masks.

63. The method of claim 62 wherein the operations further comprise determining whether a termination criterion has been reached.

64. The method of claim 63 wherein the termination criterion is whether the tinnitus mask is sufficiently optimized for the user in current conditions.

65. The method of claim 1, wherein the user's rating of the effectiveness of each presented stimulus in reducing tinnitus is received via a graphical-user interface.

66. A computer readable non-transitory memory medium embodying a program of machine-readable instructions executable by a digital processing apparatus to perform a method for generating optimized tinnitus masks, the method comprising the following operations:
presenting stimuli in succession to a user;
receiving the user's rating of the effectiveness of each presented stimulus in reducing tinnitus;
selecting a subset of the stimuli to maintain as tinnitus masks;
generating variant stimuli from the subset of the stimuli that is maintained as tinnitus masks;
storing tinnitus masks generated from the variant stimuli in a non-transitory memory medium of a secondary device; and,
supplying the tinnitus masks from the secondary device.

67. A system for alleviating the effects of tinnitus, the system comprising:
a first device comprising:
a non-transitory memory storage;
a processor coupled to the storage, wherein the processor is configured to perform the following operations:
presenting stimuli in succession to a user;
receiving the user's rating of the effectiveness of each presented stimulus in reducing tinnitus;
selecting a subset of the stimuli to maintain as tinnitus masks;
generating variant stimuli from the subset of the stimuli that is maintained as tinnitus masks; and
second device comprising:
a non-transitory memory storage configured to accept the tinnitus masks generated from the variant stimuli.

68. The computing system of claim 67, wherein the computing system is configured to store the stimuli and the tinnitus masks, and algorithms for searching through the tinnitus masks.

69. A method for optimizing tinnitus masks, the method comprising the following operations:
identifying a set of parent tinnitus masks;
generating a set of offspring tinnitus masks;
storing the offspring tinnitus masks in a non-transitory memory medium;
receiving a rating of the effectiveness of each offspring tinnitus mask in reducing tinnitus;
determining whether to terminate the process; and,
in response to terminating the process, storing the offspring tinnitus masks in a non-transitory memory medium of a secondary device.

70. The method of claim 69, wherein the operation of generating a set of offspring tinnitus masks includes utilizing self-adaptation of evolutionary parameters associated with evolution of tinnitus masks, to optimize performance.

71. The method of claim 69, wherein the operation of determining whether to terminate the process comprises determining whether a termination criterion has been reached.

72. The method of claim 69, wherein the operation of determining whether to terminate the process comprises determining whether a user is satisfied with the level of optimization.

73. The method of claim 69, wherein the operations further comprise selecting, based on the ratings of effectiveness of the offspring tinnitus masks, a subset of the set of offspring tinnitus masks, to utilize to generate a subsequent generation set of offspring tinnitus masks.

74. The method of claim 69, wherein the operation of generating a set of offspring tinnitus masks comprises varying one or more parameters of each parent tinnitus mask.

75. The method of claim 69, wherein the operation of generating a set of offspring tinnitus masks comprises random variation of parent tinnitus masks.

76. The method of claim 69, wherein the operation of generating a set of offspring tinnitus masks comprises directed variation of the parent tinnitus masks.

77. The method of claim 76, wherein the directed variation comprises methods of modification of the parent tinnitus masks using a Gaussian distribution.

78. The method of claim 76, wherein the directed variation comprises combining parts of at least two parent tinnitus masks.

79. The method of claim 76, wherein the directed variation comprises combining at least two parent tinnitus masks.

80. The method of claim 78, wherein combining parts includes averaging across parent tinnitus masks.

81. The method of claim 78, wherein the parts of the at least two parent tinnitus masks are combined based on a function of the parent tinnitus masks.

82. The method of claim 69, wherein the operation of generating a set of offspring tinnitus masks comprises introducing new tinnitus masks.

83. The method of claim 69, wherein the operation of generating a set of offspring tinnitus masks comprises reintroducing old tinnitus masks.

84. The method of claim 69, wherein the operation of generating a set of offspring tinnitus masks comprises downloading tinnitus masks from a database.

85. The method of claim 69, wherein the operation of generating a set of offspring tinnitus masks is user derived based upon tinnitus masks presented to the user.

86. A computer readable non-transitory memory medium embodying a program of machine-readable instructions executable by a digital processing apparatus to perform a method for optimizing tinnitus masks, the method comprising the following operations:
   identifying a set of parent tinnitus masks;
   generating a set of offspring tinnitus masks;
   receiving a rating of the effectiveness of each offspring tinnitus mask in reducing tinnitus;
   determining whether to terminate the process; and,
   in response to terminating the process, storing the offspring tinnitus masks in a non-transitory memory medium of a secondary device.

87. A method for the collection and sharing of tinnitus masks, the method comprising the following operations:
   a first device uploading tinnitus masks to a non-transitory memory database, where the tinnitus masks are optimized for use by a first user;
   downloading from the database, the optimized tinnitus masks developed by the first user, for use by a second user; and
   utilizing the downloaded optimized tinnitus masks in the optimization of personalized tinnitus masks, to accelerate the search for personalized tinnitus masks that alleviate second user suffering.

88. The method of claim 87, wherein the downloaded optimized tinnitus masks are randomly selected.

89. The method of claim 87, wherein the downloaded optimized tinnitus masks are specifically selected.

90. The method of claim 87, wherein the operations further comprise paying a fee to access the database.

91. The method of claim 87, wherein the operations further comprise uploading personal information.

92. A computer readable non-transitory memory medium embodying a program of machine-readable instructions executable by a digital processing apparatus to perform a method for the collection and sharing of tinnitus masks, the method comprising the following operations:
   a first device uploading tinnitus masks to a database, where the tinnitus masks are optimized for use by a first user;
   downloading from the database, the optimized tinnitus masks developed by the first user, for use by a second user; and
   utilizing the downloaded optimized tinnitus masks in the optimization of personalized tinnitus masks, to accelerate the search for personalized tinnitus masks that alleviate second user suffering.

* * * * *